(12) United States Patent
Brosnan et al.

(10) Patent No.: US 8,537,344 B2
(45) Date of Patent: Sep. 17, 2013

(54) WATER COLOR SENSING HARDWARE AND METHODOLOGY FOR APPLIANCES

(75) Inventors: Daniel Vincent Brosnan, Louisville, KY (US); James Quentin Pollett, Louisville, KY (US)

(73) Assignee: General Electric Company, Schenectady, NY (US)

( * ) Notice: Subject to any disclaimer, the term of this patent is extended or adjusted under 35 U.S.C. 154(b) by 277 days.

(21) Appl. No.: 12/946,322

(22) Filed: Nov. 15, 2010

(65) Prior Publication Data
US 2012/0120386 A1 May 17, 2012

(51) Int. Cl.
*G01N 21/00* (2006.01)

(52) U.S. Cl.
USPC ................................ 356/51; 356/72; 356/442

(58) Field of Classification Search
USPC ...... 356/72–73, 132, 436, 440–442, 402–425
See application file for complete search history.

(56) References Cited

U.S. PATENT DOCUMENTS

| | | | |
|---|---|---|---|
| 6,844,934 B2 * | 1/2005 | Retzlaff et al. | 356/436 |
| 7,113,280 B2 | 9/2006 | Oon et al. | |
| 7,400,407 B2 * | 7/2008 | Ng et al. | 356/442 |
| 7,491,366 B2 * | 2/2009 | Tokhtuev et al. | 422/82.05 |
| 2004/0135089 A1 * | 7/2004 | Manz et al. | 250/343 |
| 2007/0046942 A1 | 3/2007 | Ng et al. | |
| 2008/0317628 A1 * | 12/2008 | Ishibashi et al. | 422/55 |
| 2009/0098022 A1 * | 4/2009 | Tokhtuev et al. | 422/82.05 |
| 2009/0231581 A1 * | 9/2009 | Han et al. | 356/341 |
| 2009/0262351 A1 * | 10/2009 | Erickson et al. | 356/409 |
| 2010/0200756 A1 * | 8/2010 | Maiden | 250/357.1 |

FOREIGN PATENT DOCUMENTS

WO WO2010/051906 5/2010

OTHER PUBLICATIONS

Bloomberg, Dan. Color Quantization. Sep. 4, 2008, Leptonica p. 5 chp2.4.*
Dunn "Whirlpool Duet Washing Machine Water Recycling and Reduction Project". Apr. 15, 2008, p. 6 & 26.*
Bloomberg, Dan. "Color Quantization Using Octrees". Leptonic, 2008 p. 4-5.*

* cited by examiner

*Primary Examiner* — Gregory J Toatley
*Assistant Examiner* — Maurice Smith
(74) *Attorney, Agent, or Firm* — Dority and Manning, P.A.

(57) ABSTRACT

Apparatus and methodologies are provided to selectively activate a liquid usage option in a washing apparatus based on the color of the liquid. Light from different light sources is passed through a liquid to be tested and the intensity of the light passing through the liquid is measured. The measurement is adjust based on a measurement of the turbidity of the liquid and the measurement compared to a reference value derived from measurements of a clear liquid. A decision is made based on the adjust measured color of the liquid regarding retention of the liquid for further use in the washing apparatus. The liquid tested may correspond to grey water from a previous wash cycle.

15 Claims, 6 Drawing Sheets

| Ref # | RED | GREEN | BLUE |
|---|---|---|---|
| 1 | 0% | 0% | 0% |
| 2 | 0% | 0% | 25% |
| 3 | 0% | 0% | 50% |
| 4 | 0% | 0% | 75% |
| 5 | 0% | 0% | 100% |
| 6 | 0% | 25% | 0% |
| 7 | 0% | 25% | 25% |
| 8 | 0% | 25% | 50% |
| 9 | 0% | 25% | 75% |
| 10 | 0% | 25% | 100% |
| 11 | 0% | 50% | 0% |
| 12 | 0% | 50% | 25% |
| 13 | 0% | 50% | 50% |
| 14 | 0% | 50% | 75% |
| 15 | 0% | 50% | 100% |
| 16 | 0% | 75% | 0% |
| 17 | 0% | 75% | 25% |
| 18 | 0% | 75% | 50% |
| 19 | 0% | 75% | 75% |
| 20 | 0% | 75% | 100% |
| 21 | 0% | 100% | 0% |
| 22 | 0% | 100% | 25% |
| 23 | 0% | 100% | 50% |
| 24 | 0% | 100% | 75% |
| 25 | 0% | 100% | 100% |
| 26 | 25% | 0% | 0% |
| 27 | 25% | 0% | 25% |
| 28 | 25% | 0% | 50% |
| 49 | 25% | 100% | 75% |
| 50 | 25% | 100% | 100% |
| 51 | 50% | 0% | 0% |
| 74 | 50% | 100% | 75% |
| 75 | 50% | 100% | 100% |
| 76 | 75% | 0% | 0% |
| 99 | 75% | 100% | 75% |
| 100 | 75% | 100% | 100% |
| 101 | 100% | 0% | 0% |
| 124 | 100% | 100% | 75% |
| 125 | 100% | 100% | 100% |

900

1000

WATER COLOR SENSING HARDWARE AND METHODOLOGY FOR APPLIANCES

FIELD OF THE INVENTION

The present subject matter relates to color sensing in appliances. More particularly, the present subject matter relates to color sensing of previously used or "grey water" in appliances.

BACKGROUND OF THE INVENTION

In a typical laundry cycle the user will fill the tub with a laundry load and the machine will wash and rinse the load several times. A typical cycle may have 1 or more separate rinses and spinouts in which you would expect the wastewater to get progressively cleaner with each rinse.

In water reuse the concept is to save the water from any portion of the wash cycle, including but not limited to the last rinse, as this water would be the cleanest of any of the otherwise waste water, and then use it as either wash or rinse water in the next clothing load.

It is therefore very important to detect multiple characteristics of this grey water such as microbial content, color and turbidity, bleach content, etc.

In view of these known concerns it would be advantageous to provide a apparatus and methodology to accurately determine the color and turbidity of the grey water to prevent damaging clothing unintentionally should the wastewater be reused.

BRIEF DESCRIPTION OF THE INVENTION

Aspects and advantages of the invention will be set forth in part in the following description, or may be obvious from the description, or may be learned through practice of the invention.

The present subject matter relates to methodologies provided for selecting usage options for a liquid in a washing appliance. The method provides a plurality of different light sources and directs light from the light sources through a liquid to be tested. The light intensity received from each of the sources is measured after passing through the liquid. The turbidity within the liquid is also measured and the values of the measure light intensities are adjusted based on the measured turbidity. A selection from a plurality of water usage options is made based on the adjusted values.

In certain embodiments red, green, and blue light sources are provided and measurements are made by a light sensor paired with each of the light sources. In other embodiments a single light sensor is used and in particular embodiments an adjustment is made to the measured light values based on the angle of incidence of the light from the plurality of sensors onto the single sensor.

In other embodiments, the method provides for measuring turbidity using infrared light by directing light from the infrared light sources through a liquid to be tested and measuring the infrared light intensity received after passing through the liquid. Selected embodiments provided for establishing a reference value for light levels based on the measuring light intensity received after passing through a clear liquid. In certain embodiments, the method determines whether to dump the liquid or to keep and possibly treat it for later use.

In particular embodiments, the method establishes a plurality of light quantization levels so that measuring the light intensity received from each of the sources after passing through the liquid corresponds to assigning a measurement value corresponding one of the quantization levels. In particular such embodiments, the method established five quantization levels.

The present subject matter also relates to apparatus for selecting usage options for a liquid in a washing appliance. The apparatus includes a chamber for holding a liquid to be tested. There are also provided a plurality of different light sources configured to shine light through the liquid toward at least one light sensor. A turbidity sensor is provided to measure turbidity within the liquid and a controller is provided to receive signals from the at least one light sensor and the turbidity sensor and to adjust the values of the signals from the light sensor based on the measured turbidity. The controller will then activate a usage option based on the adjusted values.

In particular embodiments, the apparatus includes a source of clear liquid and a grey water storage tank. In such embodiments, the controller is further configured to establish color reference levels based on measured light levels through the clear liquid and to measure light levels after passing through grey water from said grey water storage tank. The controller then selectively operates either a valve or a pump to selectively dump, treat, or keep the grey water for later use.

These and other features, aspects and advantages of the present invention will become better understood with reference to the following description and appended claims. The accompanying drawings, which are incorporated in and constitute a part of this specification, illustrate embodiments of the invention and, together with the description, serve to explain the principles of the invention.

BRIEF DESCRIPTION OF THE DRAWINGS

A full and enabling disclosure of the present invention, including the best mode thereof, directed to one of ordinary skill in the art, is set forth in the specification, which makes reference to the appended figures, in which.

Figure 1:
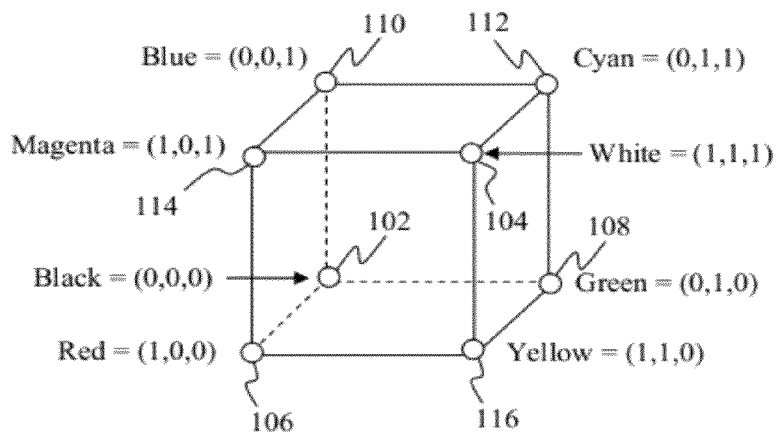
FIG. 1 is a cubical representation of a Red-Green-Blue (RGB) color space.

Repeat use of reference characters throughout the present specification and appended drawings is intended to represent same or analogous features or elements of the invention.

DETAILED DESCRIPTION OF THE INVENTION

Reference now will be made in detail to embodiments of the invention, one or more examples of which are illustrated in the drawings. Each example is provided by way of explanation of the invention, not limitation of the invention. In fact, it will be apparent to those skilled in the art that various modifications and variations can be made in the present invention without departing from the scope or spirit of the invention. For instance, features illustrated or described as part of one embodiment can be used with another embodiment to yield a still further embodiment. Thus, it is intended that the present invention covers such modifications and variations as come within the scope of the appended claims and their equivalents.

Figure 12:
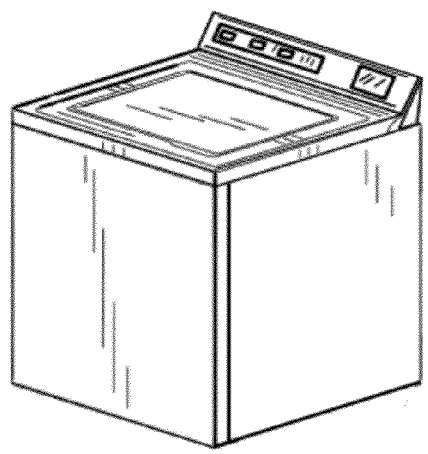
FIG. 12 is a representation of a washing appliance in which the present subject matter may be employed.

As noted in the Summary section, the present subject matter is directed toward color sensing of previously used or "grey water" in appliances such as the washing appliance illustrated in FIG. 12.

Figure 2:
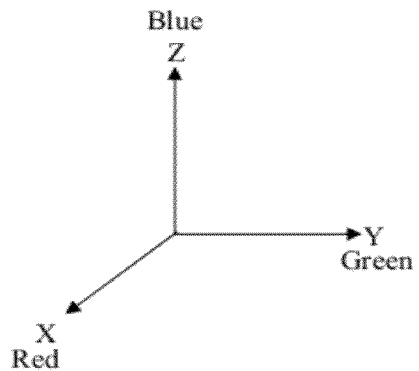
FIG. 2 is a Cartesian coordinate representation of the RGB color space of FIG. 1.

Referring now to FIGS. 1 and 2, the visible spectrum is the portion of the electromagnetic spectrum that is visible to the human eye. Electromagnetic radiation in this range of wavelengths is called visible light or simply light. A typical human eye will respond to wavelengths from about 390 to 750 nm. Typically the eye is most sensitive to light at about 555 nm, generally corresponding to the green region of the optical spectrum. The spectrum does not, however, contain all the colors that the human eyes and brain can distinguish. Unsaturated colors such as pink, or purple variations such as magenta, are absent, for example, because they can only be made by a mix of multiple wavelengths.

The RGB color space is the best-known and most widely used color model. In RGB each color is represented by three values red (R), green (G) and blue (B), positioned along the axes of the Cartesian coordinate system as illustrated in FIG. 2. The values of RGB are assumed to be in the range of [0,1] or in some cases in the range of [0-255]. In this way black may be represented as (0, 0, 0), and white as (1, 1, 1) or, in alternate scales, as (255, 255, 255). These black and the white colors are represented in FIG. 1 by two of the opposite corner 102, 104 of cube 100 that can be defined by the R, G, B axes of the Cartesian coordinate systems illustrated in FIG. 2. Other corners of cube 100 represent the red (106), green (108), blue (110), cyan (112), magenta (114) and yellow (116) colors. Grayscale colors may be represented with identical R, G, B components.

Figure 3:
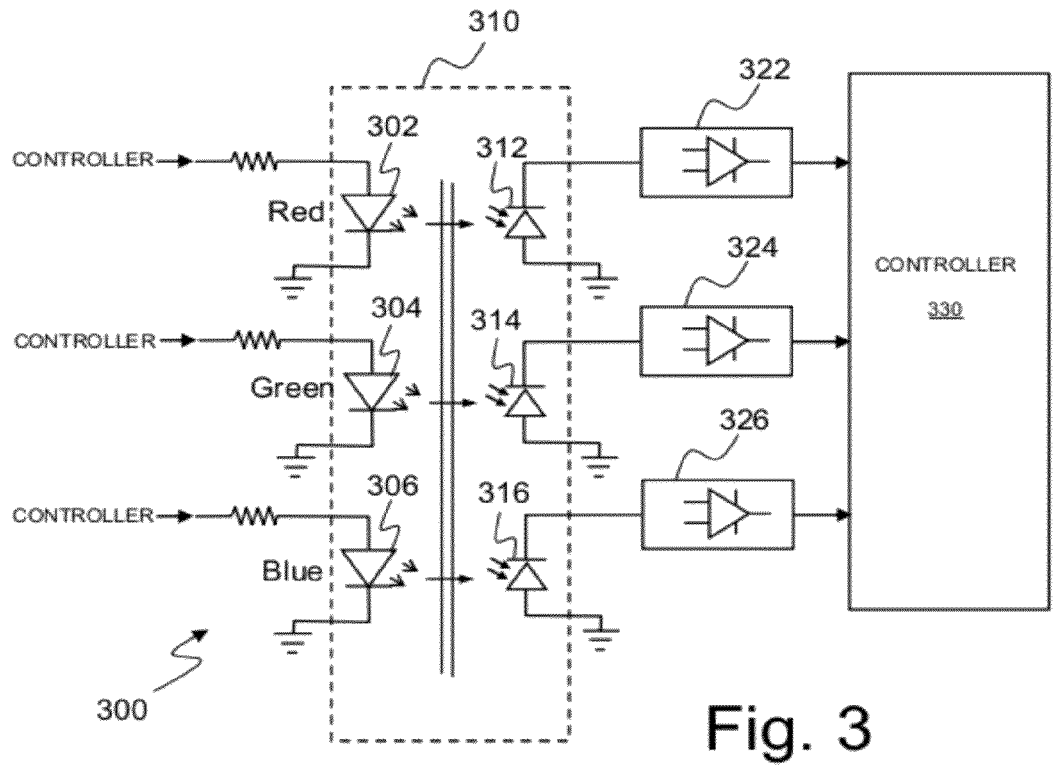
FIG. 3 is a schematic diagram of a first embodiment of an RGB detector circuit in accordance with present technology.

With reference to FIG. 3, there is illustrated a schematic diagram of a first embodiment of an RGB detector circuit 300 in accordance with present technology. The hardware used to detect color in accordance with present technology consist of an array of photo-emitters 302, 304, 306 on one side of a chamber 310 and an array of photo-detectors 312, 314, 316 on the opposite side. In one embodiment, RED, GREEN, and BLUE Light Emitting Diodes (LEDs) may be used as the photo-emitters 302, 304, 306 and photo-diodes as the photo-detectors 312, 314, 316. The selection of these colors is made as the present technology uses calculations based on the RGB Color Space.

LEDs 302, 304, 306 are controlled by a controller that can alter their brightness, duty cycle, and timing. The photo-diode signal is boosted through an op-amp network 324, 322, 326 and the resulting signals are fed into controller 330 for processing.

The medium, whether it be "clear reference fluid" or "filter medium" will act as a lens, allowing certain light frequencies to pass while blocking others. The medium would act as a "spatial filter" in this example. Theoretically the "clear" condition will allow all frequencies to pass unimpeded. In practice there will typically be some impedance, which will be accounted and corrected for in software for any condition.

In the instance of a clear condition when one of the colored LEDs 302, 304, 306 is turned on at a certain intensity, the output on the detector side will be at 100% for that color. When in a filter condition the output will be reduced based on the type, that is, color of the medium. In a further alternative configuration, it is possible to use actual colored LEDs as the detector and not emitter because they will work similarly and are more sensitive at the color they would normally emit.

An example of this is when in CLEAR condition, when LEDs 302, 304, 306 are turned on individually the OUTPUT=100% for each color. In an exemplary circuit, the 100% output level may correspond to about 4 Volts DC. When a colored lens such as a dyed water enters the chamber 310 the medium characteristics change. In an instance where the medium is slightly red colored it would be expected that the RED output should remain around 100% while the BLUE and GREEN outputs will drop to, for example, around 80%. The values of each color intensity/output drop permits approximation of the true color of the liquid.

Figure 4:
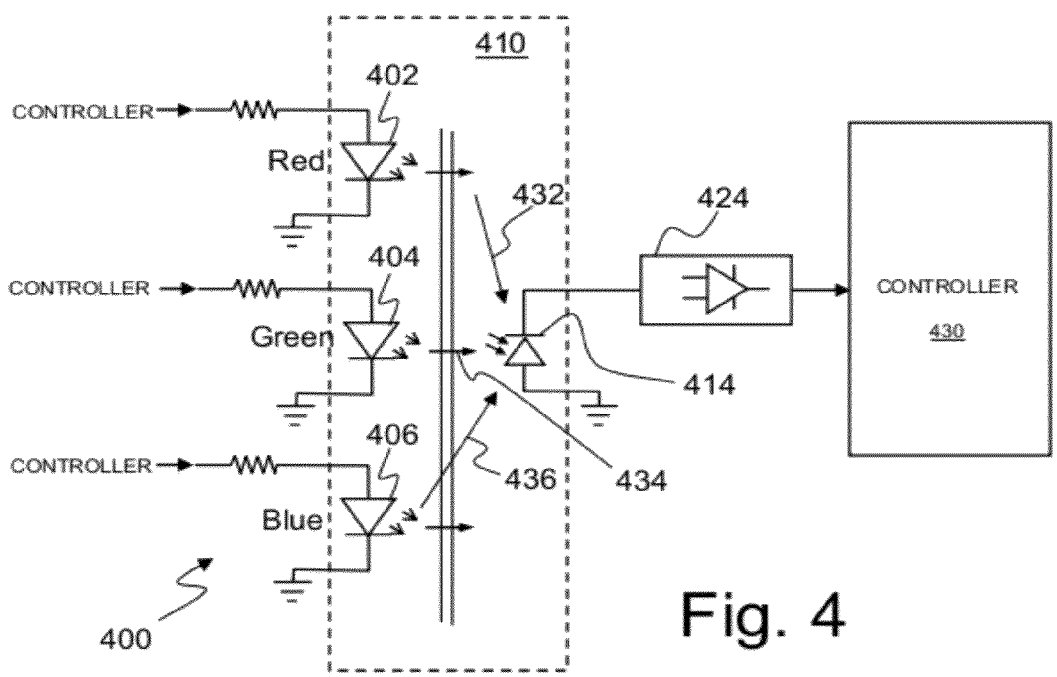
FIG. 4 is a schematic diagram of a second embodiment of an RGB detector circuit in accordance with present technology.

There are several ways of implementing this principle concept including using only one photo-detector and compensating for the angle of each LED in relation to the photo-detector. FIG. 4 illustrates such an alternate embodiment of an RGB detector circuit 400 in accordance with present technology. As may easily be seen from a comparison of FIGS. 3 and 4, the embodiment illustrated in FIG. 4 is identical to that of FIG. 3 except that the FIG. 4 embodiment uses only a single photo-detector 414 to measure the outputs of the photo-emitters 402, 404, 406. In this instance, controller 430 may be configured to operate LEDs 402, 404, 406 sequentially and to compensate for the angles of incidence of light represented by arrows 432, 434, 436 onto the single photo-detector 414. Single op-amp circuit 424 then amplifies the received light signal from photo-detector 414 and passes the amplified signal on to controller 430.

Within the context of the embodiments of both FIGS. 3 and 4, those of ordinary skill in the art should appreciate that the transmitters can be any combination of colored LEDs and the receivers can be multiple different components such as photo-diodes, photo-transistors, IC detectors, LEDs in reverse, etc.

Figure 5:
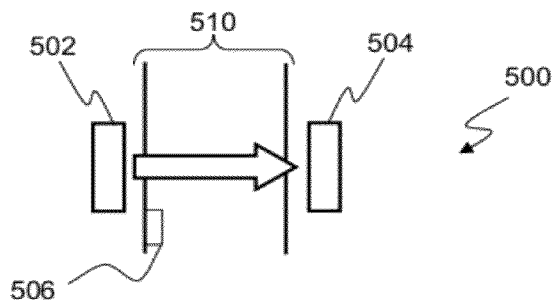
FIG. 5 is a schematic diagram of a turbidity detector.
Figure 6:
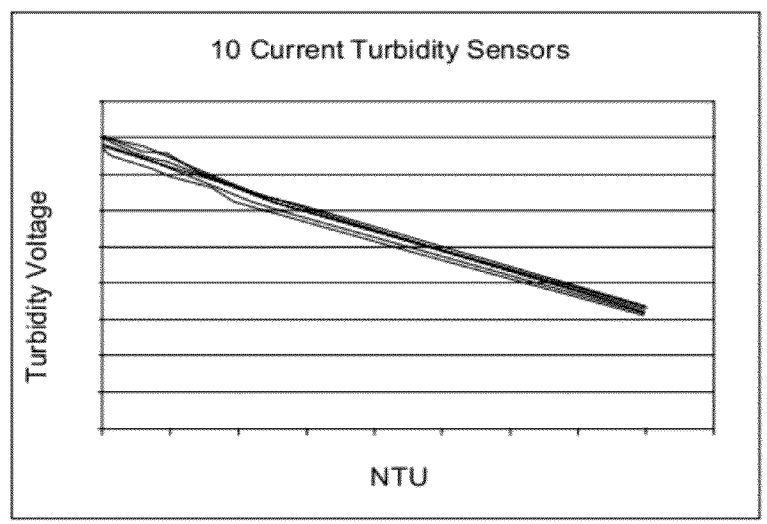
FIG. 6 is a graphical representation of the output voltage of a turbidity sensor vs. Nephelometric Turbidity Unit (NTU) for ten representative turbidity sensors.
Figure 7:
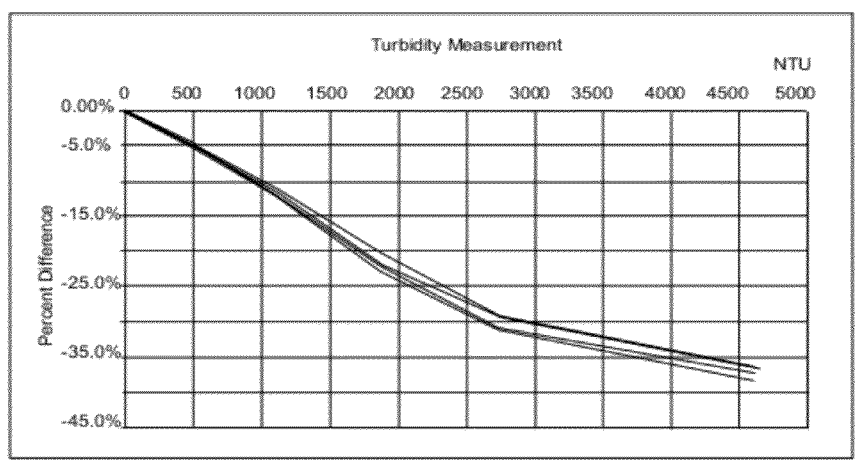
FIG. 7 is a graphical representation of percent differences vs. turbidity measurements for the sensors of FIG. 6.

With reference now to FIGS. 5, 6, and 7, aspects of the present subject matter relating to turbidity detection will now be described. FIG. 5 illustrates a schematic diagram of hardware corresponding to a turbidity detector 500 in accordance with present technology. The turbidity hardware 500 used is similar to turbidity sensors used in dishwasher and laundry systems currently and in principle is the same as described above but it utilizes infrared light from, for example, an infrared producing LED 502 so it is unaffected by the visible color spectrum. It is also put in line with the chamber 510 and its measurements not only give a reading of turbidity but also provides a measurement that is utilized in the to compensate the color calculations which will be discussed further below.

Turbidity within the context of laundry water reuse systems is most likely caused by, but not limited to, lint and fabric fibers in the water. The output of the turbidity sensor 504 will be a DC voltage and, in an exemplary configuration may range from 0 V to about 4 VDC. In this exemplary configuration, 4VDC output from sensor 504 would correspond to a clear condition while 0VDC would correspond to a maximum turbid condition. In certain embodiments of the present subject matter, a temperature sensor 506 may be provided as a part of turbidity sensor 500 to provide temperature feedback that can be used to calibrate the system under different temperature conditions.

Referring now to FIGS. 6 and 7, charts 600 and 700 illustrate the relationships between turbidity and sensor output.

FIG. 6 graphically illustrates a chart 600 of representative output voltages for an exemplary group of ten turbidity sensors. Graph 600 is presented in terms of turbidity sensor output voltage vs. Nephelometric Turbidity Units (NTU). FIG. 7 illustrates a chart 700 of representative percent differences vs. turbidity measurements given in Nephelometric Turbidity Units (NTU) for the sensors represented in FIG. 6.

Figure 8:
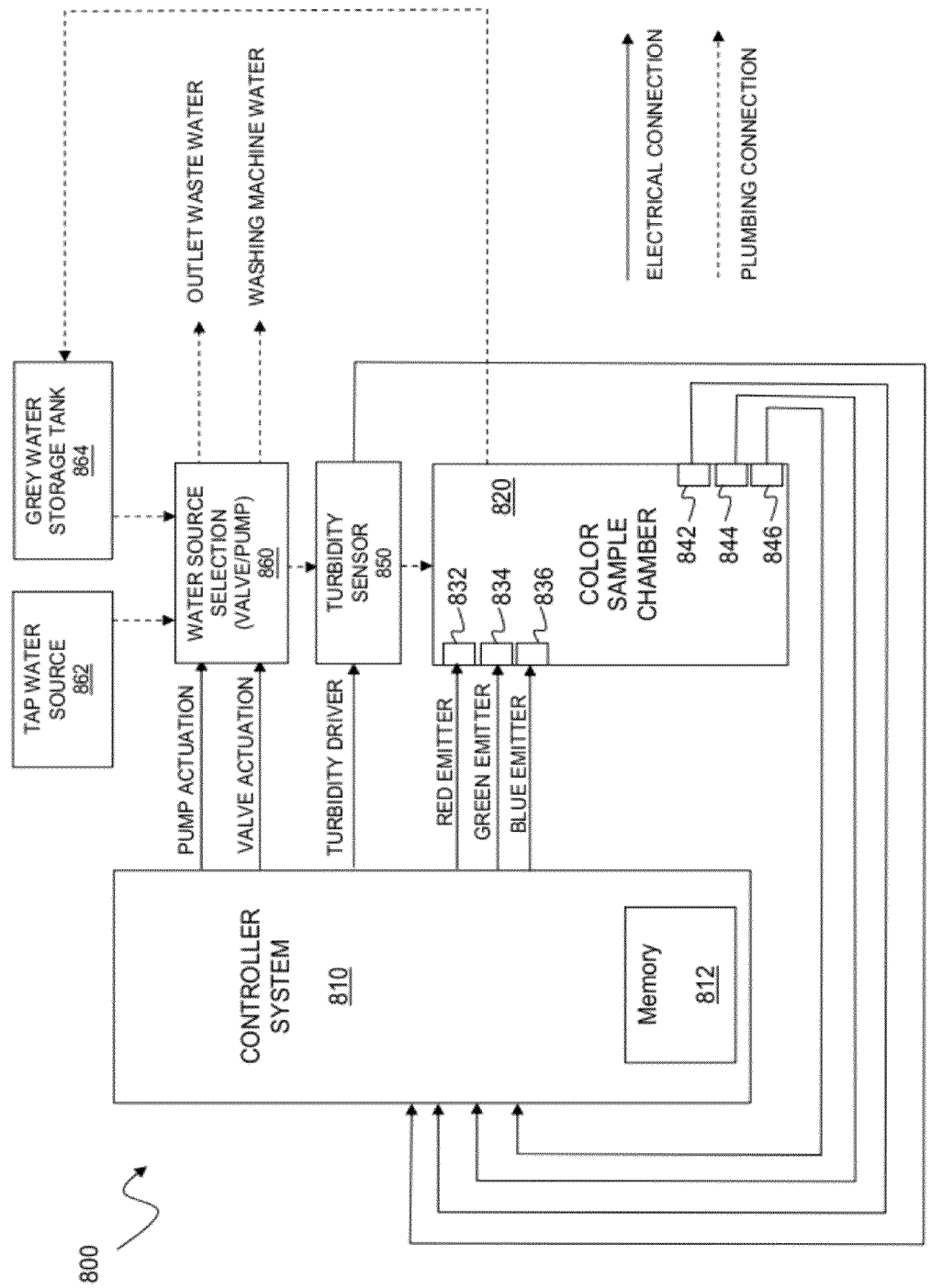
FIG. 8 is a schematic representation of a water color detection circuit in accordance with present technology.

Referring now to FIG. 8, there is illustrated a schematic representation of a water color detection circuit 800 in accordance with present technology. The hardware of the system may be completely integrated and includes a controller system 810, a sample chamber 820, light emitters 832, 834, 836, one or more light detectors 842, 844, 846, a turbidity sensor 850, a tap water source 862, a grey water storage tank 864 and associated plumbing, valves, and pumps (not separately numbered). Controller system 810 may include a storage device corresponding to a memory 812. Memory 812 may also be provided as a separate entity within the overall system.

Those of ordinary skill in the art will appreciated that while the system may be configured as a completely integrated package, other options are possible. Such options may include, for example without limitation, the use of a personal type computer or other software and/or hardware driven computational device operating as controller system 810. The controller system 810 may also be constructed using application specific integrated circuit (ASIC) device.

In whatever manner the hardware portion of the system is implemented, the overall system, never-the-less, relies on a controller system in order to drive components, receive and analyze feedback, and then take actions based on the feedback analyzed. Implementation of such systems given the present level of disclosure herein is deemed to be well within the capabilities of those of ordinary skill in the art and thus will not be further described.

Figures 9, 10:
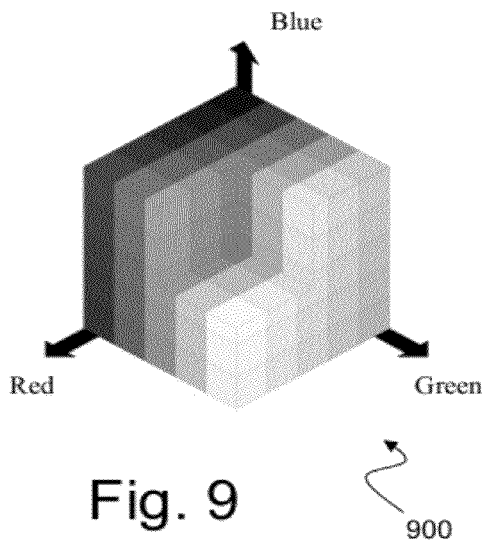
FIG. 9 is a color cube representation of an RGB color approximation space in accordance with present technology.
FIG. 10 is a color matrix lookup table of representative RGB percentiles for each of the colors represented in FIG. 9.

Referring now to FIGS. 9 and 10, there is illustrated in FIG. 9 a color cube representation 900 of an RGB color approximation space in accordance with present technology and in FIG. 10 a chart 1000 of representative RGB percentiles for each of the colors represented in FIG. 9. In general the control associated with color sensing takes a light intensity measurement of a known medium, for example, clear tap water, and compares it to the light intensity of a filter medium, for example, discolored water, for Red, Green, and Blue light. The filter mediums output may be less for at least some of the colors than the clear tap water. By comparing these two results a percentage may be calculated which indicates the amount of light intensity of each color being filtered by the filter medium. Using these percentages and applying to the RGB color scheme an approximation of the filter color can be achieved.

In accordance with present disclosure, a few assumptions may be made. The first is that RGB [0,0,0] equates to completely BLACK while RGB[1,1,1] is CLEAR, that is, not white. Secondly, all points where R=G=B, such as RGB[0.5, 0.5,0.5] are considered to be grayscale shades which grow darker as you approach RGB[1,1,1].

As previously noted, in some color scales, the scale for colors ranges form 0-255. Because the present technology is configured for local, as opposed to online, calculations, a lookup table may be created in software and stored in a memory which contains "all colors." In reality, not all colors are seen continuously but rather are seen in discrete levels. For example, if colors are quantize in levels from 0 to 255 there would be produced a color cube of length, width, and height 255 which would consist of $255^3$=16581375 individual cubes of discrete color. This number is quite large so that in practice to conserve memory space and complexity while still meeting system performance requirements the quantization level can be brought down to below 255 or higher if precise resolution is required at the cost of memory.

Referring to FIG. 9, there is illustrated a cube 900 with quantization levels 0-4. These five levels may be considered to be equivalent to 0%, 25%, 50%, 75%, and 100% color intensity output such that there are $5^3$=125 discrete colors that can be referenced. Cube 900 and associated color matrix lookup table 1000 may be implemented in software as appropriate for a particular implementation of the present technology. It should be appreciated that while this particular embodiment provides for a reduced quantization level of 125 discrete colors for the color cube, other scales and quantization levels can be provided to meet resolution demand of any particular system. The more levels provided, the more colors that can be approximated. With reference to FIG. 10, it will be appreciated that color matrix lookup table 1000, in order to avoid unnecessary clutter, does not list all 125 different combinations of colors, but the percentage of RGB colors for all 125 should, never-the-less, be quite evident to those of ordinary skill in the art based on the illustrated progression.

This reduced quantization level scheme will work for all transparent liquids with some level of coloring. However, laundry system, as described herein, will often encounter turbid conditions which can result in unreliable color approximations. In accordance with present technology, in order to compensate for such turbid conditions a turbidity measurement may be taken and then mathematically apply the results to accurately sense the true color and turbidity.

Figure 11:
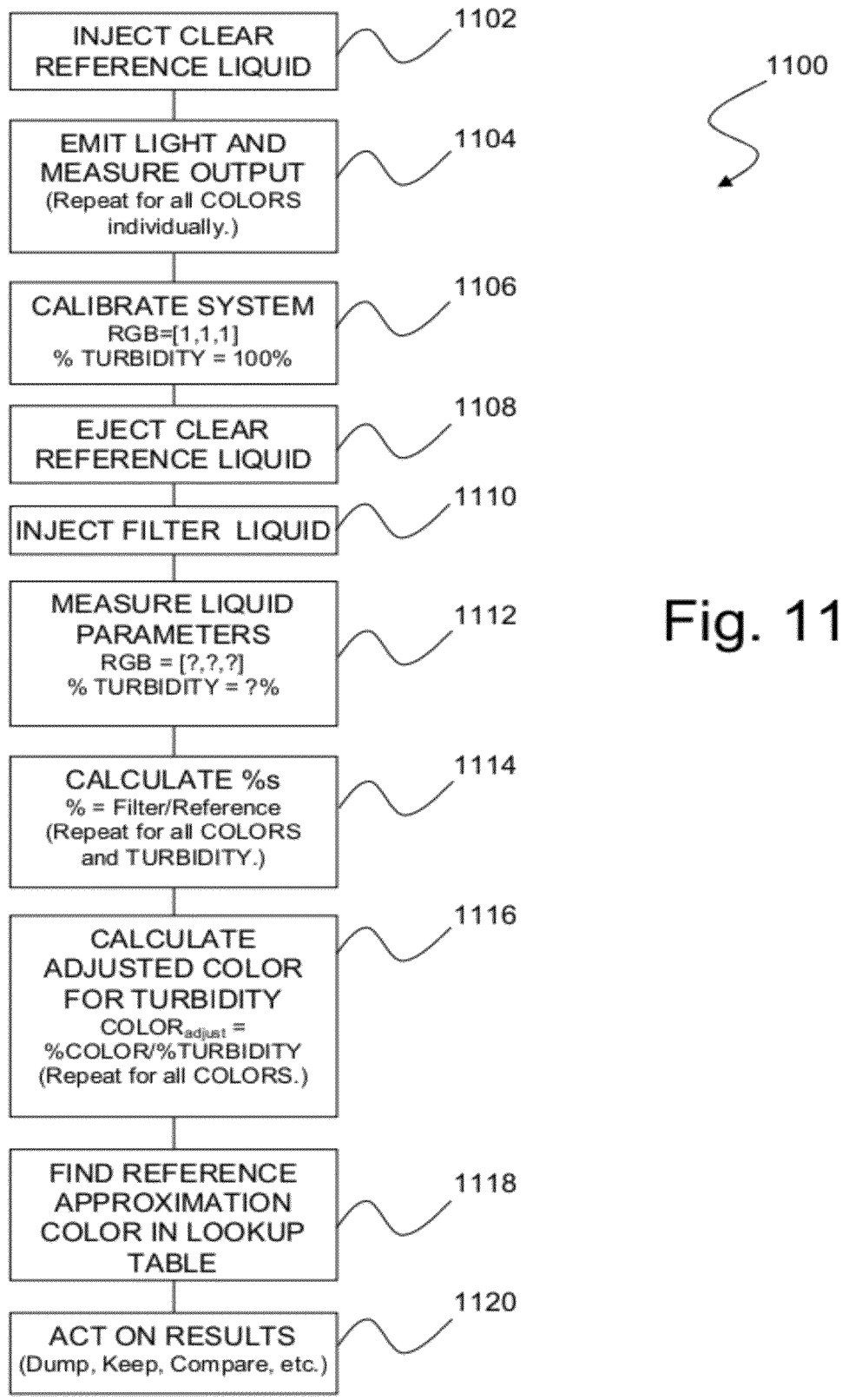
FIG. 11 is a flow chart of a method in accordance with present technology.

Referring to FIG. 11 there is illustrated a flow chart 100 of a method in accordance with present technology. In accordance with present technology, it has been appreciated that turbidity in the system will cause inaccurate color approximations. While the system will accurately detect the color of a liquid that is not turbid using color sensing methodologies alone, turbidity compensation is needed for most cases where the liquid will be at least somewhat turbid.

Turbidity is the measure of how cloudy, or how much material, is in a liquid. So in the instance of a laundry environment, lint, soils, detergents, etc could all add to system turbidity. Because the present technology uses photo-optics to emit and receive light to provide intensity measurements, system turbidity could introduce errors in intensity measurements and hence calculations and color approximations, since the turbid material may block some elements of the light.

The color sensing methodology of the present technology relies on the color of the medium alone to block elements and frequencies of light between the photo-emitters and photo-detectors. Given that a turbid condition would also block these frequencies, regardless of color, the system should be configured to compensate for the turbid condition. In accordance with present technology, this may be accomplished through the use of a turbidly sensor 500 as previously discussed with reference to FIG. 5. In a manner and similar to the way color intensity is measured in the visible spectrum turbidity content may be measured by examining the infrared spectrum intensity that can pass through a medium. The infrared light will be impeded only by turbidity and not the color of the liquid.

In this manner the system is made aware of how turbid the liquid is and can calculate a percentage decrease in the output due to the turbidity. Because the turbidity will effect all visible colors equally, the amount of intensity that is lost due to turbidity needs to be added back to the color-detectors. In accordance with present technology, a percentage of output lost due to turbidity to all color intensity measurements will be restored to obtain a true and accurate approximation of color. This turbidity correction may be made using the equation:

COLOR(adjusted)=%COLOR/%TURBIDITY

For example if %TURBIDITY=80% and %RED=50% the adjusted color approximation for RED due to error caused by turbidity would be:

Red(adjusted)=%RED/%TURBIDITY

Red(adjusted)=50/80=62.5%

This difference of 12.5% between the observed RED intensity and the adjusted RED intensity is caused by the amount of turbidity in the water and if not corrected would cause a great deal of error in the color approximation.

Consider another example where the measured color percent output intensities are RGB [0.329, 0.706, 0.176] or in the rounded 255 scale, RGB [84, 180, 45]. Without turbidity compensation, the color sensing methodology would approximate the color incorrectly. In accordance with present technology, however, when examining the contribution of turbidity it may be found that the percent turbidity is measured at 75%. This means that there is a 25% decline in the entire scale of light intensity output for all colors of 25%. Compensation for this decline should be made as follows:
%TURBIDITY=75%
%RED=32.9%
%GREEN=70.6%
%BLUE=17.6%
Red(adjusted)=%RED/%TURBIDITY
Red(adjusted)=32.9/75=43.4%
GREEN(adjusted)=%GREEN/%TURBIDITY
GREEN(adjusted)=70.6/75=94.1%
BLUE(adjusted)=%BLUE/%TURBIDITY
BLUE(adjusted)=17.6/75=23.5%

With turbidity compensation in accordance with present technology, the color sensing parameters become RGB [0.434, 0.941, 0.235] or in the rounded 255 scale RGB [112, 240, 60]. Through the implementation of the present technology, an accurate means of measuring color and turbidity is obtained such that the washer control system can take proper actions with respect to decisions including such as whether to save and/or treat the rinse water for further use or to dump the water.

An embodiment of the present invention can also be embodied in the form of computer program code, for example, whether stored in a storage medium, loaded into and/or executed by a computer, or transmitted over some transmission medium, such as over electrical wiring or cabling, through fiber optics, or via electromagnetic radiation, wherein, when the computer program code is loaded into and executed by a computer, the computer becomes an apparatus for practicing the invention. When implemented on a general-purpose microprocessor, the computer program code segments configure the microprocessor to create specific logic circuits. The technical effect of the executable code is to facilitate prediction and optimization of modeled devices and systems.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they include structural elements that do not differ from the literal language of the claims, or if they include equivalent structural elements with insubstantial differences from the literal languages of the claims.

What is claimed is:

1. A method for selecting usage options for each of a plurality of cycles of grey water from a washing appliance, comprising:
providing a plurality of different light sources; and
for each of a plurality of cycles of grey water, performing operations comprising;
directing light from the plurality of light sources through the grey water
measuring the light intensity received from each of the plurality of light sources after passing through the grey water;
measuring turbidity within the grey water;
adjusting the values of the measured light intensities based on the measured turbidity; and
selecting from a plurality of water usage options an option for reuse of the liquid in the washing appliance based on the adjusted values.

2. A method as in claim 1, wherein providing a plurality of different light sources comprises: providing a red, green, and blue light source.

3. A method as in claim 1, wherein measuring the light intensity from each of the sources comprises:
pairing individual light sensors with each of the plurality of light sources; and
measuring the light at each light sensor from its paired light source.

4. A method as in claim 1, wherein measuring the light intensity from each of the light sources comprises:
providing a single light sensor configured to receive light from each of the plurality of light sources; and
measuring light at the single light sensor from each of the plurality of light sources.

5. A method as in claim 4, further comprising:
adjusting the measured value of light received from individual light sources based on the incidence angle of the light from the light source onto the light sensor.

6. A method as in claim 1, wherein measuring turbidity comprises:
providing an infrared light source;
directing light from the infrared light sources through a liquid to be tested; and
measuring the infrared light intensity received after passing through the liquid.

7. A method as in claim 1, further comprising:
directing light from the plurality of light sources through a clear liquid;
measuring the light intensity received from each of the plurality of light sources after passing through the clear liquid; and
establishing a reference value based on the measured light intensity received after passing through the clear liquid.

8. A method as in claim 1, wherein the plurality of water usage options include at least dumping the water, treating the water, or keeping the water for later use.

9. A method as in claim 1, further comprising:
establishing a plurality of light quantization levels so that measuring the light intensity received from each of the plurality of light sources after passing through the liquid corresponds to assigning a measurement value corresponding one of the quantization levels.

10. A method as in claim 9, wherein establishing a plurality of light quantization levels comprises establishing five quantization levels.

11. Apparatus for selecting usage options for each of a plurality of cycles of grey water from a washing appliance, comprising:
a chamber for holding the grey water to be tested;
a plurality of different light sources disposed to direct light through the grey water to be tested;
at least one light sensor configured to produce signals based on light received from the plurality of different light sources through the grey water to be tested;
a turbidity sensor configured to measure turbidity within the grey water to be tested;
a controller configured to perform operations with respect to each of the plurality of cycles of grey water, the operations comprising:
receiving signals from the at least one light sensor and the turbidity sensor,
adjusting the values of the signals from the light sensor based on the measured turbidity, and
activating a usage option for the grey water in the washing appliance based on the adjusted values.

12. Apparatus as in claim 11, wherein said plurality of different light sources comprises red, green, and blue light source.

13. Apparatus as in claim 11, wherein said turbidity sensor comprises an infrared light source and sensor configured to measure infrared light passing through the grey water.

14. Apparatus as in claim 11, further including,
a source of clear liquid; and
a grey water storage tank,
wherein said controller is further configured to:
establish color reference levels for each of said plurality of different light sources by causing the light from said plurality of different light sources to be measured by said at least one light sensor after passing through clear liquid from said source of clear liquid;
cause light from said plurality of different light sources to be measured by said at least one light sensor after passing through grey water from said grey water storage tank;
compare said adjusted values to said color reference levels; and
selectively dump, treat, or keep the grey water for later use.

15. Apparatus as in claim 11, further comprising:
a storage device storing data corresponding to a plurality of light quantization levels for each of the plurality of different light sources; and
wherein said controller is further configured to assigning a measurement value corresponding one of the quantization levels.

* * * * *

UNITED STATES PATENT AND TRADEMARK OFFICE
CERTIFICATE OF CORRECTION

| | | |
|---|---|---|
| PATENT NO. | : 8,537,344 B2 | Page 1 of 1 |
| APPLICATION NO. | : 12/946322 | |
| DATED | : September 17, 2013 | |
| INVENTOR(S) | : Brosnan et al. | |

It is certified that error appears in the above-identified patent and that said Letters Patent is hereby corrected as shown below:

On the title page, item 52, under "U.S. Cl.", in Column 1, Line 1, delete "356/72;" and insert -- 356/73; --, therefor.

In the claims

In Column 8, Line 15, in Claim 1, delete "grey water" and insert -- grey water; --, therefor.

Signed and Sealed this
Second Day of February, 2016

Michelle K. Lee
*Director of the United States Patent and Trademark Office*